United States Patent
Lynglev et al.

(10) Patent No.: US 8,153,396 B2
(45) Date of Patent: Apr. 10, 2012

(54) METHOD FOR PRODUCING A CASEIN HYDROLYSATE

(75) Inventors: Gitte Budolfsen Lynglev, Frederiksberg (DK); Per Munk Nielsen, Hilleroed (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/992,918

(22) PCT Filed: May 29, 2009

(86) PCT No.: PCT/EP2009/056644
§ 371 (c)(1),
(2), (4) Date: Nov. 16, 2010

(87) PCT Pub. No.: WO2009/147105
PCT Pub. Date: Dec. 10, 2009

(65) Prior Publication Data
US 2011/0097760 A1    Apr. 28, 2011

Related U.S. Application Data

(60) Provisional application No. 61/058,231, filed on Jun. 3, 2008.

(30) Foreign Application Priority Data

Jun. 3, 2008 (EP) .................... 08157453

(51) Int. Cl.
*C12P 21/06* (2006.01)
(52) U.S. Cl. .................................................. 435/68.1
(58) Field of Classification Search .................. None
See application file for complete search history.

(56) References Cited

U.S. PATENT DOCUMENTS

2001/0026797 A1 * 10/2001 Sjoeholm et al. ............ 424/94.6

FOREIGN PATENT DOCUMENTS

| WO | WO 88/03947 A1 | 6/1988 |
|---|---|---|
| WO | WO 94/25580 A1 | 11/1994 |
| WO | WO 96/13174 * | 5/1996 |
| WO | WO 98/27827 A1 | 7/1998 |
| WO | WO 98/31239 A1 | 7/1998 |
| WO | WO 99/05918 A1 | 2/1999 |
| WO | WO 01/58276 A2 | 8/2001 |
| WO | WO 03/007730 A1 | 1/2003 |
| WO | WO 2004/072279 A2 | 8/2004 |
| WO | WO 2004/111220 A1 | 12/2004 |
| WO | WO 2004/111222 A1 | 12/2004 |
| WO | WO 2004/111223 A1 | 12/2004 |
| WO | WO 2005/115445 * | 12/2005 |
| WO | WO 2005/123911 A2 | 12/2005 |

* cited by examiner

*Primary Examiner* — Nashaat Nashed
(74) *Attorney, Agent, or Firm* — Elias Lambris

(57) ABSTRACT

The present invention relates to a method for producing a casein hydrolysate using a microbial endopeptidase.

18 Claims, No Drawings

SEQUENCE LISTING

<160> NUMBER OF SEQ ID NOS: 1

<210> SEQ ID NO 1
<211> LENGTH: 188
<212> TYPE: PRT
<213> ORGANISM: Nocardiopsis species.

<400> SEQUENCE: 1

```
Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185
```

# METHOD FOR PRODUCING A CASEIN HYDROLYSATE

CROSS-REFERENCE TO RELATED APPLICATIONS

This application is a 35 U.S.C. 371 national application of PCT/EP2009/056644 filed May 29, 2009, which claims priority or the benefit under 35 U.S.C. 119 of European application No. 08157453.5 filed Jun. 3, 2008 and U.S. provisional application No. 61/058,231 filed Jun. 3, 2008, the contents of which are fully incorporated herein by reference.

REFERENCE TO A SEQUENCE LISTING

This application contains a sequence listing in computer readable form. The computer readable form is incorporated herein by reference.

TECHNICAL FIELD

The present invention relates to a method for producing a casein hydrolysate using a microbial endopeptidase.

BACKGROUND OF THE INVENTION

Casein hydrolysates are used for protein fortification, e.g. in sports drinks, and in other dietary drinks, dry blended beverages, nutritional bars, infant formula, etc. Casein hydrolysates have in some cases been found to be less allergenic than whey protein hydrolysates which make them potentially more useful in, e.g., infant formula. Casein hydrolysates may be manufactured using proteolytic enzymes to hydrolyse the casein. In industrial manufacturing of casein hydrolysates, high solubility or suspendability of the hydrolysed protein is important both from a processing point of view, from a pure yield/economical point of view and because of mouthfeel and sensory attributes. It was therefore an object for the present inventors to identify proteolytic enzymes which are useful for preparing casein hydrolysates having a high solubility, such as a high solubility at low pH and/or a high solubility at low or moderate degree of hydrolysis.

Endopeptidases found to be applicable according to the present invention have been previously described. E.g., the endopeptidase derived from *Nocardiopsis* sp. NRRL 18262 is disclosed in WO88/03947 (here the strain is referred to as *Nocardiopsis* sp. strain 10R) and WO01/58276. Other related endopeptidases which are useful according to the invention are disclosed in WO88/03947, WO04/111220, WO04/111222, WO04/111223, WO05/123911, and WO04/072279.

SUMMARY OF THE INVENTION

The present inventors have identified endopeptidases which are found to be applicable in making casein hydrolysates having a high solubility and giving uniform suspensions. Such endopeptidases are more functionally efficient than other endopeptidases used in the art when compared to an equal amount of enzyme protein, which results in better product economy for the producers of casein hydrolysates. Consequently, the present invention relates to a method for producing a casein hydrolysate, comprising: a) adding to a composition comprising casein an endopeptidase having at least 50% identity to SEQ ID NO: 1; and b) incubating so as to hydrolyse the casein.

DETAILED DISCLOSURE OF THE INVENTION

Endopeptidase

The term endopeptidase as used herein is an enzyme that hydrolyses internal peptide bonds (has endopeptidase activity).

There are no limitations on the origin of the endopeptidase for use according to the invention. Thus, the term endopeptidase includes not only natural or wild-type endopeptidases, but also any mutants, variants, fragments etc. thereof exhibiting endopeptidase activity, as well as synthetic endopeptidases, such as shuffled endopeptidases. Genetically engineered endopeptidase variants can be prepared as is generally known in the art, e.g. by site-directed mutagenesis, by PCR (using a PCR fragment containing the desired mutation as one of the primers in the PCR reactions), or by random mutagenesis. Examples of endopeptidase variants, as used in the present context, are endopeptidases in which one or more amino acids have been deleted, inserted or substituted with other amino acids.

Examples of endopeptidases for use according to the invention are
(i) the endopeptidase derived from Nocardiopsis sp. NRRL 18262, disclosed in WO01/58276, the sequence of which is shown as SEQ ID NO: 1 of the present document;
(ii) endopeptidases having at least 50, 55, 60, 65, 70, 75, 80, 85, 90, or at least 95% amino acid identity to the endopeptidase of (i);
(iii) mutants, variants or fragments of the endopeptidases of (i) or (ii) exhibiting endopeptidase activity.

For purposes of the present invention, the alignment of two amino acid sequences can be determined by using the Needle program from the EMBOSS package available at emboss.orq) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between two amino acid sequences is calculated as the number of exact matches in an alignment of the two sequences, divided by the length of the shortest of the two sequences. The result is expressed in percent identity.

An exact match occurs when the two sequences have identical amino acid residues in the same positions of the overlap. The length of a sequence is the number of amino acid residues in the sequence (e.g. the length of SEQ ID NO: 1 is 188).

As examples of bacterial endopeptidases applicable for use according to the invention can also be mentioned the endopeptidase from *Nocardiopsis alba* (previously *Nocardiopsis dassonvillei*) NRRL 18133 disclosed in WO88/03947, the endopeptidases from *Nocardiopsis dassonvillei* subsp. *dassonvillei* DSM 43235, *Nocardiopsis alba* DSM 15647, *Nocardiopsis* sp. DSM 16424 and the synthetic Protease 22, all four disclosed in WO04/111220, the endopeptidase from *Nocardiopsis prasina* DSM 15648 disclosed in WO04/111222, the endopeptidase from *Nocardiopsis prasina* DSM 15649 disclosed in WO04/111223, the endopeptidases from *Nocardiopsis prasina* (previously *Nocardiopsis alba*) DSM 14010, *Nocardiopsis alkaliphila* DSM 44657 and *Nocardiopsis lucentensis* DSM 44048, all three disclosed in WO05/123911, the endopeptidases from *Brachysporiella gayana* CGMCC 0865, *Metarhizium anisopliae*, *Gliocladium* sp. CBS 114001, *Periconia* sp. CBS 114002, *Periconia* sp. CBS 114000 and *Curvularia lunata* CBS 114003, all 6 disclosed in WO04/072279, and mutants, variants or fragments of any of these exhibiting endopeptidase activity.

An endopeptidase for use according to the invention is a microbial endopeptidase, preferably a bacterial endopeptidase, the term bacterial indicating that the endopeptidase is derived from, or originates from, a bacteria, or is an analogue, a fragment, a variant, a mutant, or a synthetic endopeptidase derived from a bacteria. It may be produced or expressed in the original wild-type bacterial strain, in another microbial strain, or in a plant; i.e. the term covers the expression of wild-type, naturally occurring endopeptidases, as well as expression in any host of recombinant, genetically engineered or synthetic endopeptidases.

In the process of the invention, the endopeptidase may be purified. The term "purified" as used herein covers enzyme protein preparations where the preparation has been enriched for the enzyme protein in question. Such enrichment could for instance be: the removal of the cells of the organism from which an extracellular enzyme protein was produced, the removal of non-protein material by a protein specific precipitation or the use of a chromatographic procedure where the enzyme protein in question is selectively adsorbed and eluted from a chromatographic matrix. The endopeptidase may have been purified to an extent so that only minor amounts of other proteins are present. The expression "other proteins" relate in particular to other enzymes. An endopeptidase to be used in the method of the invention may be "substantially pure", i.e. substantially free from other components from the organism in which it was produced, which may either be a naturally occurring microorganism or a genetically modified host microorganism for recombinant production of the endopeptidase.

However, for the uses according to the invention, the endopeptidase need not be that pure. It may, e.g., include other enzymes, even other endopeptidases.

In a preferred aspect, the endopeptidase to be used in the method of the invention has been purified to contain at least 20%, preferably at least 30%, at least 40% or at least 50%, (w/w) of the endopeptidase in question out of total protein. The amount of endopeptidase may be calculated from an activity measurement of the preparation divided by the specific activity of the endopeptidase (activity/mg EP), or it may be quantified by SDS-PAGE or any other method known in the art. The amount of total protein may, e.g., be measured by amino acid analysis.

Use of the endopeptidase according to the present invention may be combined with use of other enzymes, e.g. other proteases. In one preferred embodiment, an endopeptidase, e.g. the one derived from Nocardiopsis sp. NRRL 18262, is combined with an exopeptidase, or a protease preparation having exopeptidase activity, e.g. a protease preparation derived from Aspergillus oryzae, as disclosed in WO94/25580, such as Flavourzyme® (Novozymes NS, Denmark).

In one particular embodiment, the endopeptidase for use according to the invention has a pH-activity optimum close to neutral, when determined by hydrolysis of casein and subsequent reaction of TCA-soluble peptides with o-phtaldialdehyde and 2-mercaptoethanol followed by measurement of the absorbance of the resulting complex at 340 nm.

The term pH-activity optimum close to neutral may mean that the endopeptidase has a pH optimum in the interval of pH 5.5-11, preferably pH 7-11, more preferably pH 8-11, even more preferably pH 9.5-10.5, and most preferably at around pH 10.

In another particular embodiment, the endopeptidase for use according to the invention is thermostable.

The term thermostable may mean that the temperature optimum at pH 9 is at least 50° C. or at least 55° C., preferably at least 60° C., more preferably at least 65° C., and even more preferably at least 67° C., such as about 70° C., when determined by hydrolysis of casein as described above.

Casein Hydrolysate

Casein in the context of the present invention is the predominant group of proteins in milk, which may account for 75-80% of all protein in milk and cheese. The soluble form of casein may be coagulated by acids and/or by rennet.

In a preferred embodiment, the casein is from cow's milk.

Casein to be used in the method of the invention may, e.g., be in the form of sodium caseinate, potassium caseinate or calcium caseinate.

In the method of the invention, the casein material is typically mixed or dispersed in water to form a slurry comprising about 1% to about 25% protein by weight. In one embodiment, the slurry may comprise about 1% to about 5% protein by weight. In another embodiment, the slurry may comprise about 6% to about 10% protein by weight. In a further embodiment, the slurry may comprise about 11% to about 15% protein by weight. In still another embodiment, the slurry may comprise about 16% to about 20% protein by weight. In still another embodiment, the slurry may comprise about 21% to about 25% protein by weight. In a preferred embodiment, the slurry may comprise about 5% to about 25% protein by weight.

After the protein material is dispersed in water, the pH and/or the temperature of the protein slurry may be adjusted so as to optimize the hydrolysis reaction, and in particular, to ensure that the endopeptidase used in the hydrolysis reaction functions near its optimal activity level. The pH of the protein slurry may be adjusted and monitored according to methods generally known in the art. The pH of the protein slurry may be adjusted at from about 5 to about 10. In one embodiment, the pH of the protein slurry may be adjusted at from about 6 to about 9. In a preferred embodiment, the pH of the protein slurry may be adjusted at from about 6.5 to about 8. The pH of the protein slurry may be maintained at such level during the hydrolysis reaction or it may be allowed to decrease as the hydrolysis reaction proceeds. The temperature of the protein slurry is preferably adjusted and maintained at from about 45° C. to about 70° C. during the hydrolysis reaction in accordance with methods known in the art. In a preferred embodiment, the temperature of the protein slurry may be adjusted and maintained at from about 63° C. to about 70° C. during the hydrolysis reaction. In general, temperatures above this range may inactivate the endopeptidase, while temperatures below or above this range tend to slow the activity of the endopeptidase.

The hydrolysis reaction is generally initiated by adding the endopeptidase to the slurry of protein material. Alternatively, the enzyme may be dispersed in water and the protein material added slowly while stirring. The latter method may be advantageous when preparing a concentrated protein slurry to avoid that the viscosity becomes too high.

Preferably, the amount of endopeptidase used in the method of the invention is from about 0.005 to about 100 AU (as defined below) per kg casein, preferably from about 0.01 to about 50 AU per kg casein, more preferably from about 0.02 to about 30 AU per kg casein.

One Anson Unit (AU) is defined as the amount of enzyme which under standard conditions (i.e. 25° C., pH 7.5 and 10 min. reaction time) digests haemoglobin at an initial rate such that there is liberated per minute an amount of TCA soluble product which gives the same colour with phenol reagent as one milliequivalent of tyrosine. When determining the AU activity, the concentration of haemoglobin may preferably be around 1.3%.

The amount of endopeptidase added to the protein material can and will vary depending upon the source of the protein material, the desired degree of hydrolysis, and the duration of the hydrolysis reaction. The amount of endopeptidase may range from about 1 mg of enzyme protein to about 5000 mg of enzyme protein per kilogram of casein. In a preferred embodiment, the amount may range from 1 mg of enzyme protein to about 1000 mg of enzyme protein per kilogram of casein. In another preferred embodiment, the amount may range from about 5 mg of enzyme protein to about 500 mg of enzyme protein per kilogram of casein.

As will be appreciated by the skilled person, the duration of the hydrolysis reaction can and will vary. Generally speaking, the duration of the hydrolysis reaction may range from a few minutes to many hours, such as, from about 30 minutes to about 48 hours.

Preferably, the treatment with endopeptidase results in a casein hydrolysate having a degree of hydrolysis (DH) from about 0.1% to about 20%, more preferably from about 0.5% to about 10% or from about 0.5% to about 8%, even more preferably from about 2% to about 8%.

The degree of hydrolysis (DH) expresses the extent of the protein hydrolysis obtained by the method. In the context of the invention, the degree of hydrolysis (DH) is defined as follows:

DH=(Number of peptide bonds cleaved/Total number of peptide bonds)×100% The skilled person will know how to measure the DH. It may, e.g., be done using a method as described in Adler-Nissen, J., 1986, Enzymatic Hydrolysis of Food Proteins, Chapter 5, pp. 122-124.

After completion of step b), the endopeptidase may be inactivated. Such inactivation may be performed by any method known in the art, e.g. by heating to at least 75° C., such as to at least 80° C. or at least 85° C.

In one embodiment, the method of the invention further comprises treatment of the casein composition with one or more additional enzymes having protease activity. Such additional proteolytic enzyme may be one or more endopeptidases and/or one or more exopeptidases.

The one or more exopeptidases may be, e.g., one or more aminopeptidases and/or one or more carboxypeptidases.

Incubation with the endopeptidase having at least 50% identity to SEQ ID NO: 1 and incubation with the one or more additional enzymes having protease activity may not be performed simultaneously. I.e., if the proteolytic enzymes do not perform at the same pH and/or the same temperature, the casein composition may be incubated with one (or more) proteolytic enzyme(s) at first, followed by optional adjustment of pH and/or temperature and subsequent incubation with the other proteolytic enzyme(s).

When using one or more additional enzymes having protease activity, the resulting casein hydrolysate may have a higher degree of hydrolysis (DH) than indicated above. It may, e.g., have a degree of hydrolysis of about 5-25%.

A casein hydrolysate obtained by the method of the invention may be used in a food product, e.g. in a beverage. A food product according to the present invention may be any product intended for human consumption. Non-limiting examples of such food products include nutrition bars, dry blended beverages, sports drinks, energy drinks and infant formula. A casein hydrolysate obtained by the method of the invention may also be used in clinical nutrition, e.g. at hospitals.

EXAMPLE 1

Comparison of hydrolysis of sodium caseinate with endopeptidase from *Nocardiopsis* sp. NRRL 18262 having the sequence shown in SEQ ID NO: 1 and Alcalase® 2.4L (Novozymes 30 A/S, Denmark)

Hydrolysis with Protease:
Protein Preparation:

Sodium caseinate, Miprodan 30 from Arla Foods, Denmark, 88% protein: 15 g+285 g water. 35 The caseinate product was suspended to a 5% w/v suspension with demineralised water (Milli Q). The water was heated to 60° C., and the protein added to the Milli Q water while stirring in a blender, 1-2 min or until the protein was suspended/solubilised.

pH Adjustment:

pH was adjusted to 8.0 with 4 N NaOH and was maintained during the hydrolysis reaction.

Enzyme Dosage:

The *Nocardiopsis* protease and Alcalase 2.4 L were dosed at 10, 50 and 100 mg enzyme protein (ep)/kg protein. Enzyme was stored on ice during handling.

Enzyme Treatment:

Temperature: 60° C. +/−1° C.
Time: 120 min.

Enzyme was added to the protein suspension on a magnetic stirrer in a water bath. Enzyme was added when the temperature in the protein solution had reached 60° C.

Heat Inactivation/Storage:

Immediately after enzyme treatment, the samples were heat treated 15 min. at 85° C. in a shaking water bath. The samples were cooled on ice and refrigerated at 4° C. over night.

After incubation at 4° C. over night solubility and degree of hydrolysis were evaluated.

Solubility:

Solubility was measured at pH 4.0 and 6.5 using a Leco FP 528 Protein/Nitrogen analyzer measuring protein and nitrogen content by a combustion method. The Nitrogen content was measured in the soluble fraction and solubility was calculated as the Nitrogen content in percentage of total dry matter content.

Degree of Hydrolysis:

Degree of hydrolysis of the suspension was measured by pH stat as described in Adler-Nissen, J., 1986, Enzymatic Hydrolysis of Food Proteins, Chapter 5, pp. 122-124.

Results:

Degree of hydrolysis:

| Protease konc (mg/kg caseinate material) | Alcalase | *Nocardiopsis* endopeptidase |
|---|---|---|
| 0 (Reference) | | 0.62 |
| 10 | 2.87 | 2.42 |
| 50 | 7.17 | 5.61 |
| 100 | 10.92 | 7.30 |

Solubility pH 6.5:

| Protease konc (mg/kg casein material) | Solubility | | Solubility/DH | |
| | Alcalase | *Nocardiopsis* endopeptidase | Alcalase | *Nocardiopsis* endopeptidase |
|---|---|---|---|---|
| 0 (Reference) | | 98.7 | | — |
| 10 | 76.5 | 92.1 | 26.7 | 38.1 |
| 50 | 79.0 | 90.3 | 11.0 | 16.1 |
| 100 | 86.9 | 95.2 | 8.0 | 13.0 |

Solubility pH 4.0:

| Protease konc (mg/kg casein material) | Solubility | | Solubility/DH | |
|---|---|---|---|---|
| | Alcalase | Nocardiopsis endopeptidase | Alcalase | Nocardiopsis endopeptidase |
| 0 (Reference) | | 5.4 | | — |
| 10 | 29.3 | 42.0 | 10.2 | 17.4 |
| 50 | 73.3 | 70.4 | 10.2 | 12.6 |
| 100 | 84.5 | 73.9 | 7.7 | 10.1 |

CONCLUSION

It is seen that at a given concentration of protease, the endopeptidase from Nocardiopsis gave similar or moderately lower degree of hydrolysis than Alcalase. However, at pH 6.5 solubility was seen to be generally higher with Nocardiopsis endopeptidase than with Alcalase both at a given protease concentration and at a given degree of hydrolysis. Also at pH 4.0, the solubility/DH was clearly higher for the hydrolysate obtained with the *Nocardiopsis* endopeptidase than for the hydrolysate obtained with Alcalase. At pH 6.5, the solubility of the unhydrolyzed control was higher than that of the hydrolyzed products. But from a functional point of view, i.e. as regards emulsifying capacity and allergenicity, it is often desirable to have a certain protein hydrolysis (increase in DH). Whereas from a sensory point of view, the DH should not be too high, as increased DH often results in increased bitterness of the casein-hydrolysates.

In addition, visual inspection revealed a uniform suspension when using Nocardiopsis endopeptidase as the catalyst while Alcalase under the given conditions was non-uniform (lump formation).

The invention claimed is:

1. A method for producing a casein hydrolysate, comprising:
   a) adding to a composition comprising from about 5% to about 25% casein an endopeptidase having at least 50% identity to SEQ ID NO: 1; and
   b) incubating so as to hydrolyze the casein, wherein the degree of hydrolysis of the casein hydrolysate is from about 0.1% to about 20%.

2. The method of claim 1, wherein the endopeptidase has at least 60% identity to SEQ ID NO: 1.

3. The method of claim 1, wherein the endopeptidase has at least 80% identity to SEQ ID NO: 1.

4. The method of claim 1, wherein the endopeptidase has at least 85% identity to SEQ ID NO: 1.

5. The method of claim 1, wherein the endopeptidase has at least 90% identity to SEQ ID NO: 1.

6. The method of claim 1, wherein the endopeptidase has at least 95% identity to SEQ ID NO: 1.

7. The method of claim 1, wherein the endopeptidase comprises the amino acid sequence of SEQ ID NO: 1.

8. The method of claim 1, wherein the endopeptidase has a pH optimum between 9.5 and 10.5.

9. The method of claim 1, wherein the endopeptidase has a temperature optimum at pH 9 of at least 60° C.

10. The method of claim 1, wherein the endopeptidase is from Nocardiopsis.

11. The method of claim 1, wherein the endopeptidase is added at a concentration of between 1 and 1000 mg enzyme protein per kg casein.

12. The method of claim 1, wherein the endopeptidase is added at an activity of between 0.01 and 50 AU per kg casein.

13. The method of claim 1, wherein the casein hydrolysate has a degree of hydrolysis of at least 2%.

14. The method of claim 1, which further comprises treatment of the casein composition with one or more additional enzymes having protease activity.

15. The method of claim 1, which further comprises treatment of the casein composition with one or more exopeptidases.

16. The method of claim 1, wherein the degree of hydrolysis of the casein hydrolysate is from about 0.5% to about 10%.

17. The method of claim 1, wherein the degree of hydrolysis of the casein hydrolysate is from about 0.5% to about 8%.

18. The method of claim 1, wherein the degree of hydrolysis of the casein hydrolysate is from about 2% to about 8%.

* * * * *